(12) United States Patent
Bashkansky et al.

(10) Patent No.: US 6,847,449 B2
(45) Date of Patent: Jan. 25, 2005

(54) METHOD AND APPARATUS FOR REDUCING SPECKLE IN OPTICAL COHERENCE TOMOGRAPHY IMAGES

(75) Inventors: Mark Bashkansky, Alexandria, VA (US); John F Reintjes, Alexandria, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 5 days.

(21) Appl. No.: 10/307,533

(22) Filed: Nov. 27, 2002

(65) Prior Publication Data

US 2004/0100631 A1 May 27, 2004

(51) Int. Cl.[7] .................................................. G01J 4/00
(52) U.S. Cl. ...................................................... 356/364
(58) Field of Search ................................ 356/364–369, 356/450, 453, 487, 489, 491, 520; 250/225–236

(56) References Cited

U.S. PATENT DOCUMENTS

| | | | |
|---|---|---|---|
| 5,155,549 A | | 10/1992 | Dhadwal |
| 5,432,607 A | * | 7/1995 | Taubenblatt ................ 356/364 |
| 5,502,561 A | | 3/1996 | Hutchins et al. |
| 5,555,087 A | | 9/1996 | Miyagawa et al. |
| 5,748,311 A | * | 5/1998 | Hamann et al. ............ 356/336 |
| 6,100,976 A | | 8/2000 | Ackerson |
| 6,377,349 B1 | * | 4/2002 | Fercher ...................... 356/450 |
| 6,381,015 B1 | * | 4/2002 | Sonehara et al. ........... 356/450 |
| 6,429,931 B1 | | 8/2002 | Karpol et al. |
| 6,710,875 B1 | * | 3/2004 | Zavislan .................... 356/364 |
| 2002/0101593 A1 | * | 8/2002 | Yang et al. ................. 356/484 |
| 2003/0053072 A1 | * | 3/2003 | Fercher et al. ............. 356/497 |
| 2003/0137669 A1 | * | 7/2003 | Rollins et al. ............. 356/479 |

OTHER PUBLICATIONS

M. Bashkansky and J. Reintjes, "Statistics and reduction of speckle in optical coherence tomography," Optics Letters, vol. 25, No. 8, Apr. 15, 2000.

M. Bashkansky et al., "Signal processing for improving field cross–correlation function in optical coherence tomography," Optics and Photonics News, vol. 19, No. 5, May 1998.

M. Bashkansky et al., "Subsurface defect detection in ceramics using an optical gated scatter reflectometer," J. Am. Ceram. Soc. vol. 79, No. 5 (1996).

M. Bashkansky et al., "Subsurface defect detection in ceramic materials using optical gating techniques," Review of Progress in Quantitative Nondestructive Evaluation, vol. 15 (1996).

M. Bashkansky et al., "Subsurface detection and characterization of Hertzian cracks in Si3N4 balls using optical coherence tomography," NDT&E international 34 (2001).

M. Bashkansky et al., "Subsurface defect detection in ceramics by high–speed high–resolution optical coherent tomography," Optical Letters, vol. 22, No. 1, Jan. 1, 1997.

* cited by examiner

*Primary Examiner*—Michael P. Stafira
(74) *Attorney, Agent, or Firm*—John J. Karasek; L. George Legg (57) ABSTRACT

A method and apparatus for reducing speckle due to MSL, without any loss of resolution, by averaging over different angles of the incident light at low input resolution, while collecting the backscattered light at a full resolution of a lens is described. The present invention allows discrimination against the speckle due to coherent MSL.

22 Claims, 6 Drawing Sheets

PRIOR ART
FIG. 1

Mean = 67, σ = 13, S/N = 5

*PRIOR ART*
FIG. 2

Mean = 67, σ = 13, S/N = 5

Mean = 65, σ = 12, S/N = 5.4

Mean = 59, σ = 7, S/N = 8.4

*PRIOR ART*

*FIG. 3*

Mean = 60, σ = 3, S/N = 20

*PRIOR ART*

METHOD AND APPARATUS FOR REDUCING SPECKLE IN OPTICAL COHERENCE TOMOGRAPHY IMAGES

BACKGROUND OF THE INVENTION

1. Field of the Invention

This invention relates to optical coherence tomography. More particularly, it relates to a method and apparatus for improving optical coherence tomography devices used for detecting scattered optical radiation from internal structures in scattering media by reducing speckle due to multiply scattered light and without any loss of resolution.

2. Description of Related Art

Optical coherence tomography (OCT) is useful for imaging through highly scattering media. OCT allows for non-invasive, non-destructive cross-sectional optical imaging of scattering media with high spatial resolution and high sensitivity. OCT is related to white light interferomtery (WLI) and low coherence domain reflectometry (LCDR). WLI is used for one or two-dimensional profiling of surfaces. LCDR is used for one-dimensional depth probing of materials. OCT is used for two or three-dimensional internal probing of both scattering and non-scattering materials. The subject of the present invention pertains to application of OCT for study of scattering materials.

By way of general background, when a low coherence light source beam is directed into a scattering medium and reflects from in-homogeneities or internal structure, a speckle pattern is observed. The speckle pattern results from interference of different components of electromagnetic radiation which originate from a coherent source but which follow different paths in reflecting or scattering to the detector. At some points, the total field reflecting from the material will add constructively and be bright, while at other points the total field will add destructively and be dark. The signal detected in a given measurement has two components. One, which we will term the direct signal, arises from light that propagates without scattering to the region of interest(ROI), that is the region of the sample that is to be imaged, and is scattered backward from the ROI to the detector. The other component, the coherent MSL, arises from light that is multiply scattered over many different paths, all of which have the same optical path length as that of the direct signal. Although the direct signal arises only from the ROI, the coherent MSL arises from a much larger volume of the sample. The two signals combine coherently to form a speckle pattern, and the individual contributions of the direct signal and the coherent MSL are indistinguishable in usual measurements.

Various methods and apparatuses for obtaining tomographic information have heretofore been proposed wherein tomographic information, such as a tomographic image, of a medium having light scattering properties, is obtained such that the medium may not be invaded. With the OCT, a low coherence light beam is split into a light beam, which is to be irradiated to a medium, and a reference light beam, and a Michelson type of interferometer is constituted by the two split light beams. Optical heterodyne detection is carried out on the interference light beam, which is obtained from the interferometer, and the intensity of a light beam scattered backwardly from the medium is thereby determined. From the intensity of the backward scattered light beam, the tomographic information at the surface of the medium or an internal portion in the medium is obtained. Tomographic information at an arbitrary internal portion in the medium can be obtained by scanning the position of the ROI in the x-y plane and varying the optical path length of the reference light to control the z position for the depth into the medium.

It is well known in the prior art how to incorporate low coherence optical interferometers into various OCT apparatus to study scattering media. In a typical prior art optical fiber embodiment of the OCT apparatus, a low coherence radiation source and a photodetector are coupled to two input ends of a 3 dB coupler. The beams of radiation transmitted from two output ends of a 3 dB coupler are transmitted to a sample medium to be tested and a reference medium, respectively. The beams from the output ends are reflected from the sample medium and the reference medium, respectively; combined by the a 3 dB coupler; and transmitted to the photodetector.

The inventors have identified the speckled appearance of an image to be an important issue concerning typical OCT measurements. The problem of speckle is especially serious in the detection of internal structures, for which the spatial scale of the speckle is comparable with that of defects in the material, such as for example, subsurface cracks in ceramics.

Since OCT relies on coherent detection, the signal usually appears in the form of the speckle. While OCT discriminates against incoherent multiply scattered light (MSL), it fails to discriminate coherent MSL from light from a region of interest (ROI) in a sample. The coherent MSL that reaches a detector within the same coherence length as light from a ROI will be detected by OCT and will contribute to the detected speckle. It is generally recognized that some form of speckle averaging can be used for speckle reduction. Xiang et al., Proc. SPIE 3196, 79 (1997); and Schmidt, Phys. Med. Biol. 42, 1427 (1997), have used an array of four detectors to average speckle patterns.

The inventors have also recognized that speckle reduction in OCT is possible when the scattered signal light is detected and averaged in more than one direction. This can be accomplished with either a finite number of detectors in parallel, or by sequential angle averaging. Although the above techniques will reduce speckle from a ROI as well as from MSL, the penalty paid for the speckle averaging is the loss of optical resolution and also slower image acquisition. For example, in order to reduce the speckle by a factor of three, a total of nine images need to be collected with the optical resolution also deteriorated by a factor of three.

Figure 1:
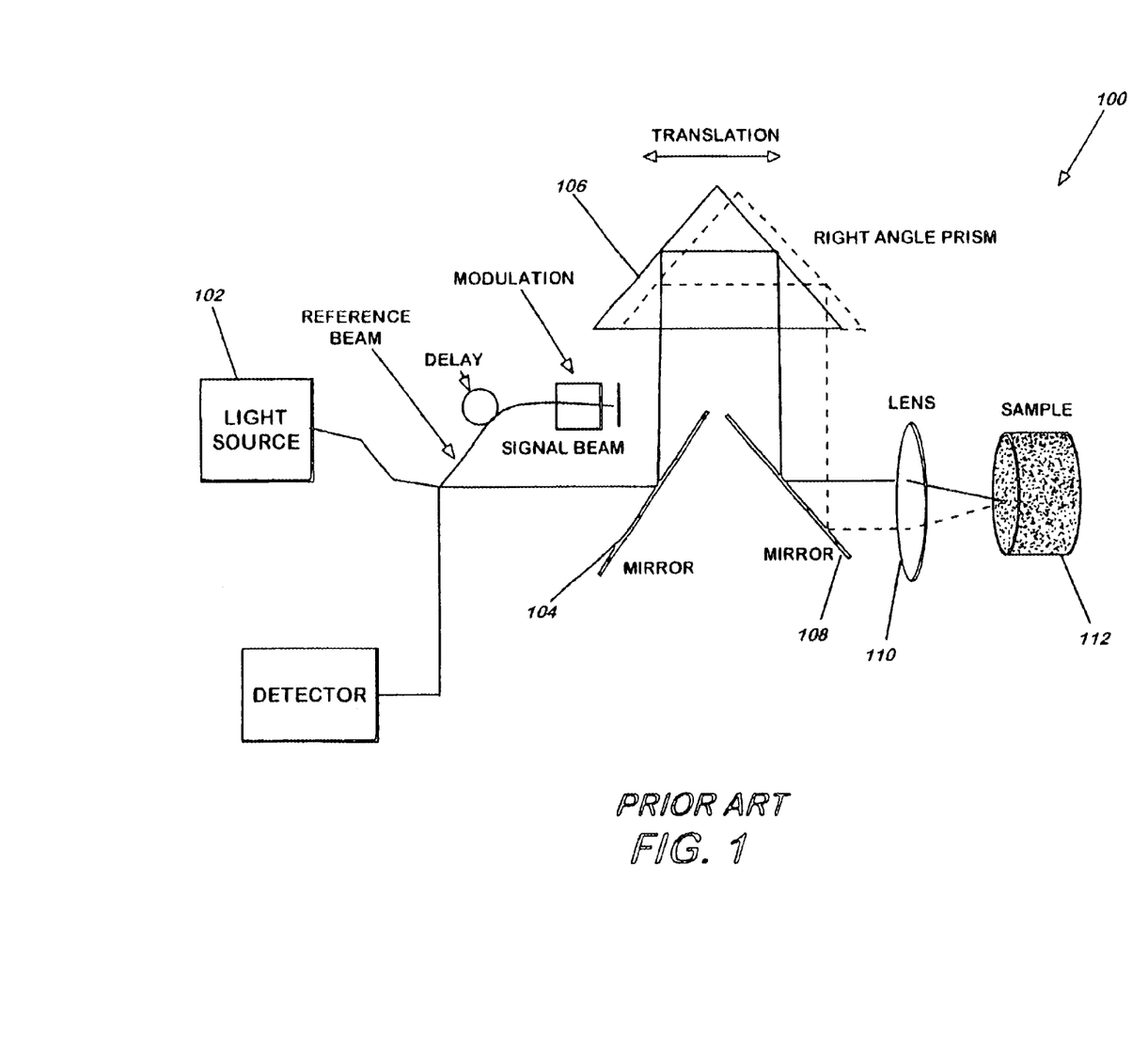
FIG. 1 is a schematic of a low-coherence fiber interferometer based system for detecting subsurface defects in ceramics with sequential angle averaging wherein signal beam translation is performed with a right-angle prism.

These techniques and the images produced by them are illustrated in FIGS. 1–4. Referring now to FIG. 1, there is shown a schematic of a low-coherence fiber interferometer based system 100 to detect subsurface defects in a sample 112. Input signal beam from a low coherence light source 102 is reflected by mirror 104, mirror 108 and is made to focus on the sample 112 via lens 110. The angle of incidence of incident light beam that is made to focus on the sample 112 is changed by translating the input signal beam in front of the lens 110 using a right angle prism 106. Translation of the prism 106 along its hypotenuse translates the input signal beam. Light scattered from the sample 112 is reflected back towards the incidence direction and completely repeats the path of the incident beam to be detected by detector 114. Scattered light is averaged over different angles of incidence of the signal beam where the signal is detected in the exact backscattered direction. Although the apparatus shown in FIG. 1 reduces speckle from a ROI as well as from coherent MSL, the penalty paid for speckle averaging is the loss of optical resolution and slower image acquisition. The loss of resolution occurs because angle averaging requires that the input beam not fill the lens. Since the return beam retraces the path of the incident beam, the resolution is determined by the relatively small diameter of the beam at the lens.

Figure 2:
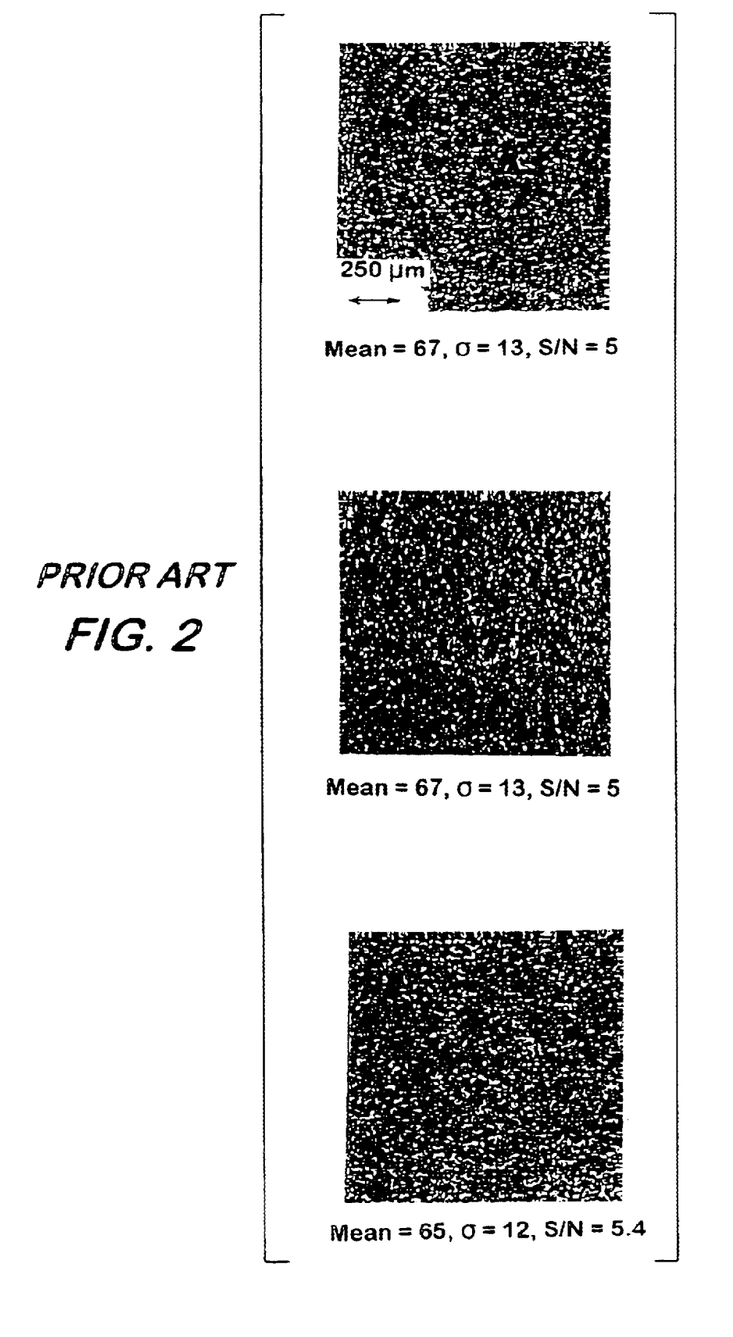
FIG. 2 is an OCT scan taken in a ceramic sample at a depth of 80 μm, as measured in air and at different angles of incidence.

FIG. 2 is an OCT scan taken at a depth of 80 μm, as measured in air and at different angles of incidence using the apparatus shown in FIG. 1. The sample used for taking the OCT scan is a flat piece of $Si_3N_4$ with a surface-penetrating Hertzian circular crack. Three representative X-Y OCT scans taken at a depth of 80 μm, as measured in air and at different angles of incidence, are shown in FIG. 2. The scan size is approximately 2.5 mm by 2.5 mm. The signal to noise ratio (SNR) was measured to be ~5. The images are observed to have a characteristic speckled appearance. The speckled appearance of the images represents a significant difficulty in crack detection.

Figure 3:
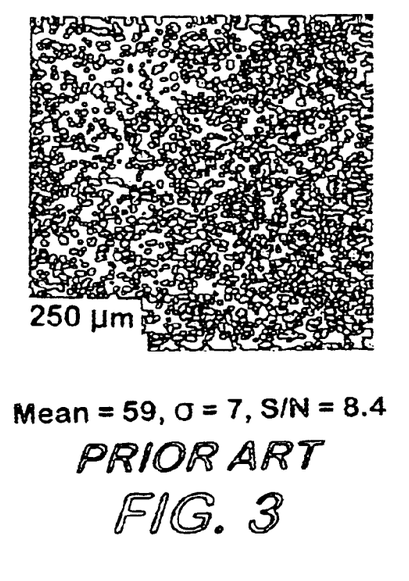
FIG. 3 is an average of eleven OCT scans such as those shown in FIG. 2, taken at one angle of incidence.

Averaged OCT images with and without changing the incidence angles were also compared. As the speckle pattern does not change from shot to shot, the averaging of the images at one incident angle merely reduces the noise without affecting the speckle. The result of 11 combined OCT scans at the same angle is shown in FIG. 3. The SNR was measured to be ~8, and the crack is still undetectable.

Figure 4:
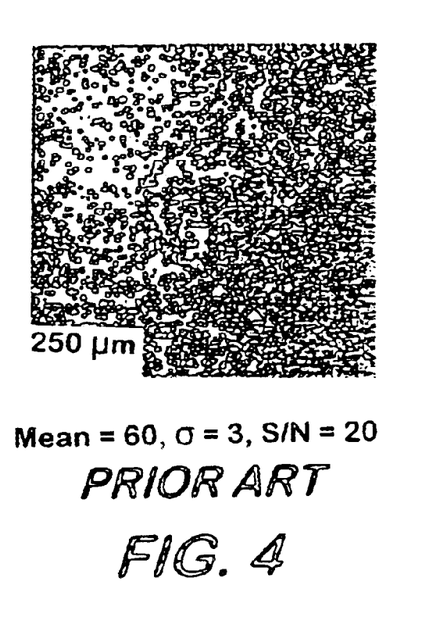
FIG. 4 is an average of eleven OCT scans such as those shown in FIG. 2, taken at different angles of incidence.

FIG. 4 shows an image illustrating the effect of speckle reduction due to averaging 11 images at different angles of incidence. The SNR was measured to be ~20. The effect of speckle reduction is directly confirmed by the clearly visible subsurface circular crack.

SUMMARY OF THE INVENTION

The present invention overcomes the above noted drawbacks encountered in the prior art. A simple and inexpensive speckle-reduction system and method is described wherein speckle averaging is performed without loss of optical resolution or reduction in image acquisition speed.

The present invention describes a method and apparatus for reducing speckle due to MSL, without any loss of resolution, by averaging over different angles of the incident light at low input resolution, while collecting the backscattered light at a full resolution of a lens. Since the incident light and the backscattered light take different input and output paths, the method of the present invention allows discrimination against the speckle due to coherent MSL.

In one aspect, the present invention relates to a method of improving quality of optical coherence tomography (OCT) images and detectability of sub-surface structures or internal structures of a sample, such as for example, scattering media. The method includes focusing incident light on the sample via a lens; reducing speckle due to detected multiply scattered light (MSL) by performing an average of the detected MSL over different angles of incident light while maintaining a constant optical path length; and collecting backscattered light from the sample at a full resolution of the lens along an output optical path which is different from optical path of the incident light.

In another aspect, the present invention provides in an optical coherence tomography (OCT) system, a method of improving quality of OCT images and detectability of sub-surface structures of a sample. The method includes focusing incident light on the sample; reducing speckled noise due to detected multiply scattered light (MSL) by performing an average of the detected MSL over different angles of incident light; and collecting backscattered light from the sample at a full resolution of a lens, focusing the incident light on the sample, along an output optical path which is different from optical path of the incident light.

In yet another aspect, the present invention provides an apparatus for improving quality of optical coherence tomography (OCT) images and detectability of sub-surface structures of a sample. The apparatus includes means for focusing incident light on the sample; means for reducing speckled noise due to detected multiply scattered light (MSL) by performing an average of the detected MSL over different angles of incident light while maintaining a constant optical path length; and means for collecting backscattered light from the sample at a full resolution of the means focusing the incident light on the sample, wherein the backscattered light is collected along an output optical path which is different from optical path of the incident light.

In a further aspect, the present invention provides an apparatus for improving quality of optical coherence tomography (OCT) images and detectability of sub-surface structures of a sample. The apparatus includes a lens for focusing incident light on the sample; a processor for reducing speckled noise due to detected multiply scattered light (MSL) by performing an average of the detected MSL over different angles of incident light while maintaining a constant optical path length; and an optical device for collecting backscattered light from the sample at a full resolution of the lens along an output optical path which is different from optical path of the incident light.

While the invention has been herein shown and described in what is presently conceived to be the most practical and preferred embodiment, it will be apparent to those of ordinary skill in the art that many modifications may be made thereof within the scope of the invention, which scope is to be accorded the broadest interpretation of the appended claims so as to encompass all equivalent methods and apparatus.

DETAILED DESCRIPTION OF THE EXEMPLARY EMBODIMENTS

Figure 5:
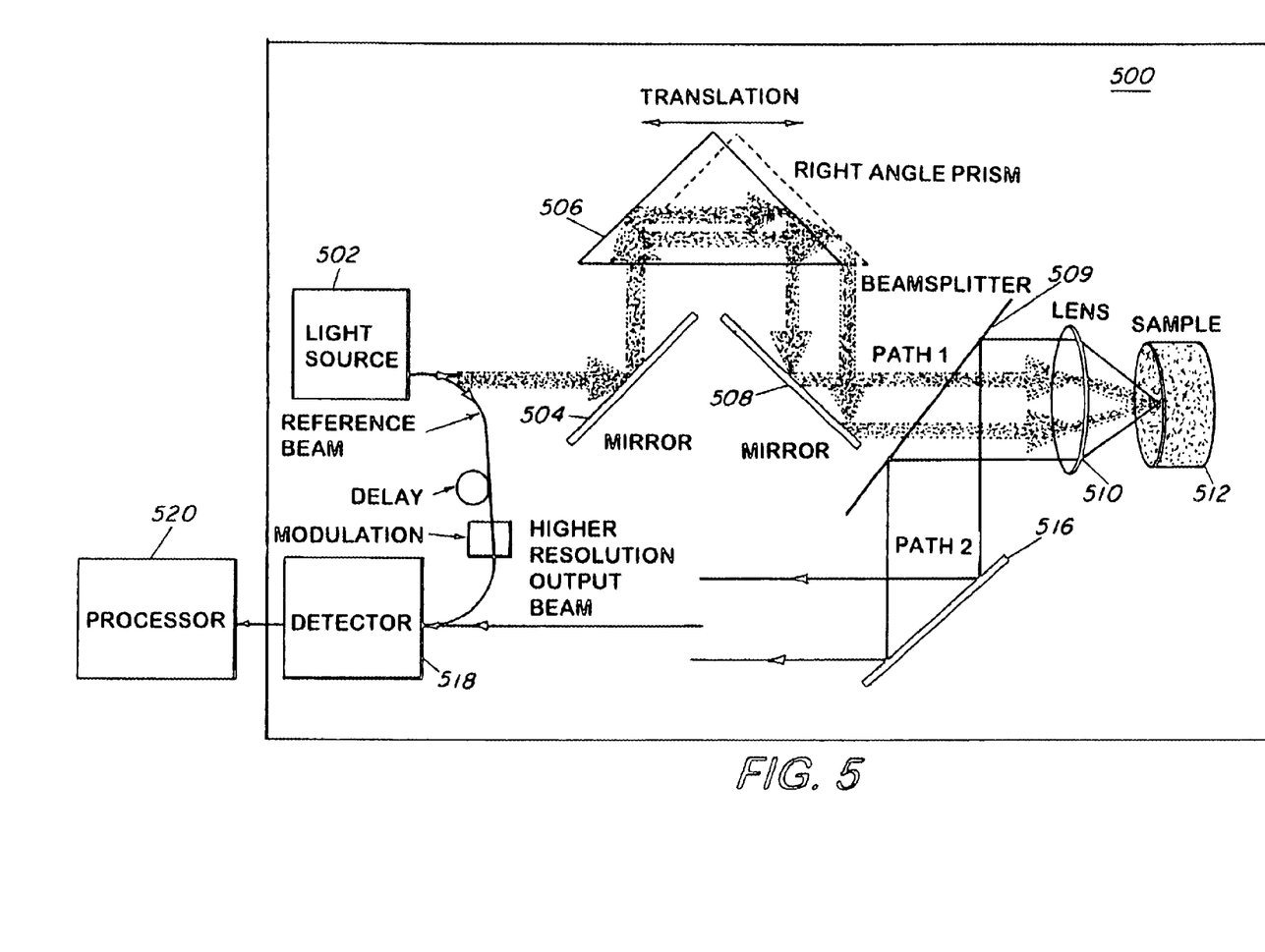
FIG. 5 is a schematic of a low-coherence fiber interferometer based system for detecting subsurface defects in a sample object in accordance with a first example embodiment of the present invention.

FIG. 5 is a schematic of a low-coherence fiber interferometer based system for detecting subsurface defects in a sample object in accordance with a first example embodiment of the present invention. Specifically, apparatus 500 is shown to include a low coherence light source 502 emitting an output beam that is split into an input signal beam and a reference beam. The input signal beam is reflected via a mirror 504 and a mirror 508. The incident light beam is then made to focus on sample 512 via lens 510. The angle of incidence of incident light beam that is made to focus on the sample 512 is changed by translating the input signal beam using a right angle prism 506 in front of the lens 510. Translation of the prism 506 along its hypotenuse translates the input signal beam while maintaining a constant optical path length of the beam.

Light scattered from the sample 512 is reflected back in the incidence direction and completely repeats the path of the incident beam to be detected by detector 514. Averaging of scattered light is performed over different angles of incidence of the incident signal beam at low input resolution, while collecting the backscattered light at a full resolution of the lens 510. The backscattered light collected at a full resolution passes through the beamsplitter 509 and is subsequently reflected by a mirror 516, and the resulting high resolution beam from the mirror 516 is interferometrically combined with the reference beam, and the two beams are subsequently detected in a detector 518. A processor 520 may be used to further process information received by the detector 518. The processor 520 may be, for example, a CPU, or a computer with information processing capability, or a distributed computing system capable of processing information to generate a user requested output. Since the output path of the scattered light, identified as PATH 2 (a high resolution path) in FIG. 5, is different from the input path of the incident light, identified as PATH 1 (a low resolution path) in FIG. 5 the apparatus of the present invention allows discrimination against the speckle due to coherent MSL. A second prism (not shown) may be employed for translation of incident light beam in another dimension.

Figure 6:
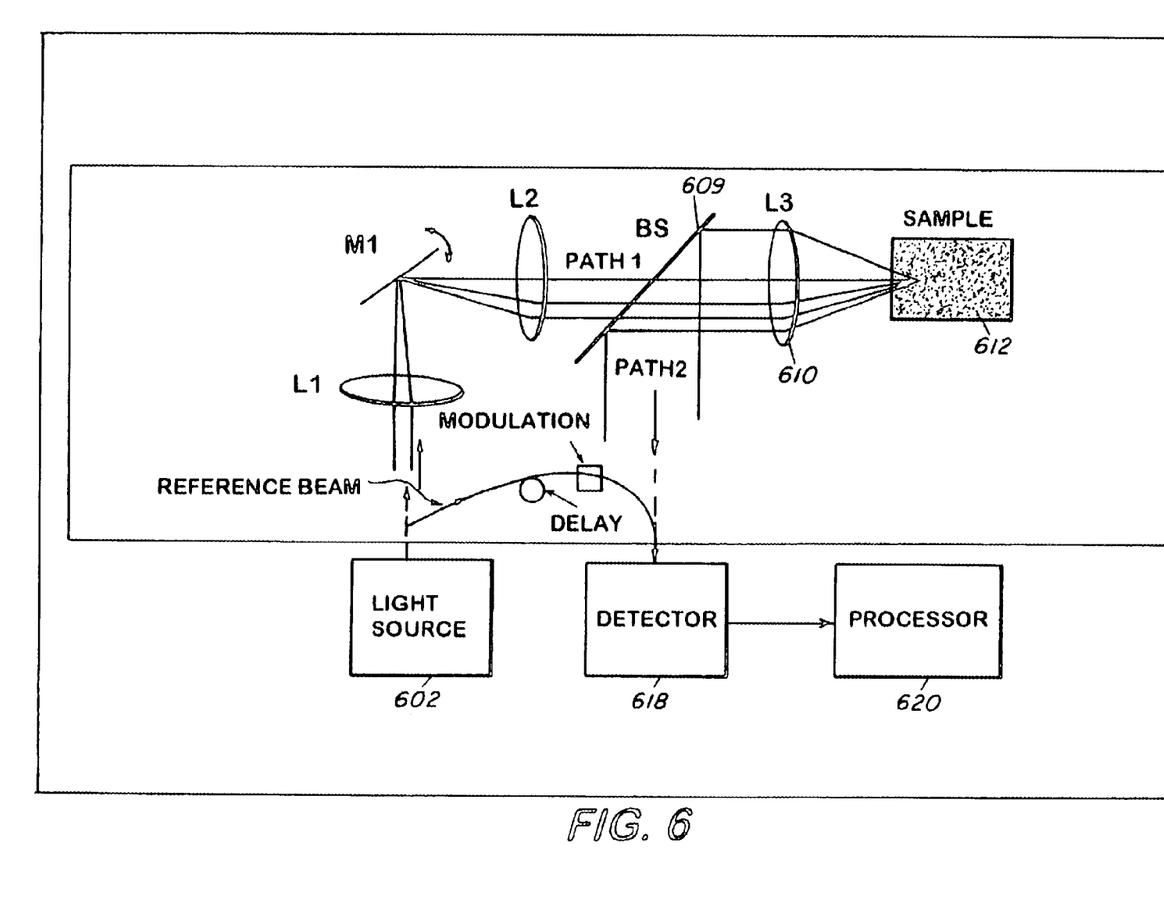
FIG. 6 is a schematic of a low-coherence fiber interferometer based system for detecting subsurface defects in a sample object in accordance with a second example embodiment of the present invention.

FIG. 6 is a schematic of a low-coherence fiber interferometer based system for detecting subsurface defects in a sample object in accordance with a second example embodiment of the present invention. The beam from light source 602 is split into a signal and reference beam as described above. A lens L1 focuses the collimated signal beam onto the center of the mirror M1 such that a tilt of the mirror M1 does not change the optical path length (OPL). A lens L2 is preferably positioned a focal length away from the mirror M1. When the mirror M1 is tilted, the beam impinging on the lens 610 is translated and focused in the sample 612 at a different angle. The backscattered light traversing along path 2 (high resolution path) is combined interferometrically with the reference beam and is detected in a detector 618. The detected information may be further processed using a processor 620, which may be similar to the processor 520 as shown in FIG. 5. As with FIG. 5, since the backscattered light traversing along path 2 is collected at a full resolution of the lens, reduction of speckle without any loss of resolution is thereby achieved in addition to achieving discrimination against the speckle due to coherent MSL. The mirror M1 may be tilted in two dimensions to increase the number of averages.

Figure 7:
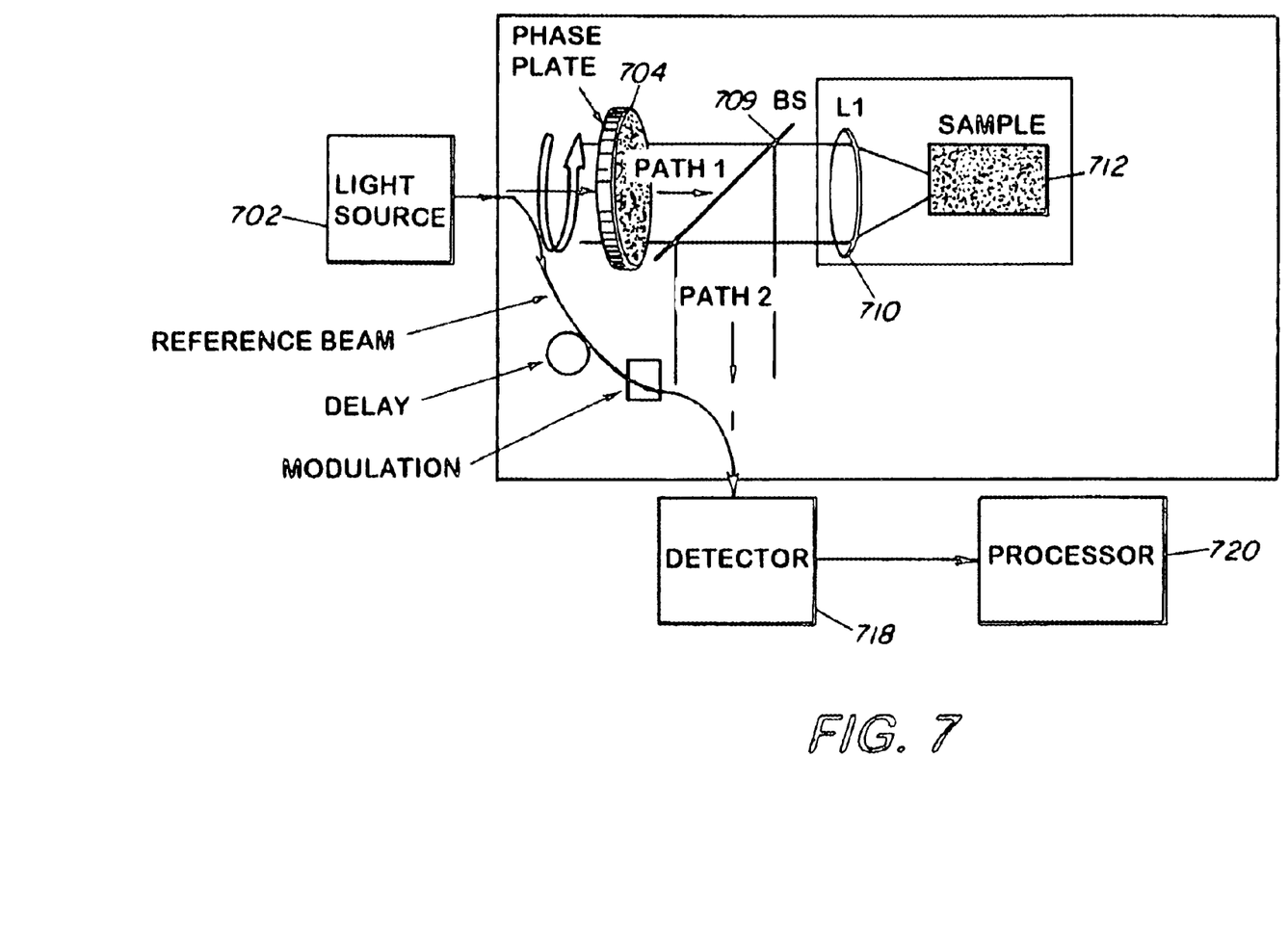
FIG. 7 is a schematic of a low-coherence fiber interferometer based system for detecting subsurface defects in a sample object in accordance with a third example embodiment of the present invention.

FIG. 7 is a schematic of a low-coherence fiber interferometer based system for detecting subsurface defects in a sample object in accordance with a third example embodiment of the present invention. The beam from light source 702 is split into an incident light beam and a reference beam as described above. A phase plate 704 is positioned in a path of the incident light beam. The phase plate 704 is rotated in order to change the angles of incidence of the incident light beam whereby the beam impinging on the lens 710 is translated and focused in the sample 712 at different angles. Further, the phase plate 704 is rotated to produce different MSL speckle for averaging. Collection of backscattered light from the sample 712 at full resolution is similar to what has been described above with respect to FIGS. 5 and 6 of the present invention.

Speckle averaging using the present invention allows retrofitting existing OCT systems. The present invention is reasonably simple, inexpensive and does not rely on the finite number of the detectors. The speckle is reduced by the square root of the number of averages. Further, no technique other than the present invention that can discriminate against the speckle due to coherent MSL is known to the inventors. Also, the present invention has the advantage of not affecting the resolution at the ROI in a sample.

The technique described in the present invention may also be combined with other known speckle reduction techniques such as, for example, polarization averaging, frequency averaging and digital signal processing. The relative translation between a sample/lens combination and the incident beam may be accomplished in different ways. The technique described in the present invention may also be applied to various scanning OCT implementations.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

BIBLIOGRAPHY

The following papers and publications are incorporated herein by reference in their entirety:

M. Bashkansky and J. Reintjes, "Statistics and reduction of speckle in optical coherence tomography," Optics Letters, Vol. 25, No. 8, Apr. 15, 2000;

M. Bashkansky et al., "Signal processing for improving field cross-correlation function in optical coherence tomography," Optics and Photonics News, Vol. 19, No. 5, May 1998;

M. Bashkansky et al., "Subsurface defect detection in ceramics using an optical gated scatter reflectometer," J. Am. Ceram. Soc. Vol. 79, No. 5 (1996);

M. Bashkansky et al., "Subsurface defect detection in ceramic materials using optical gating techniques," Review of Progress in Quantitative Nondestructive Evaluation, Vol. 15 (1996);

M. Bashkansky et al., "Subsurface detection and characterization of Hertzian cracks in Si3N4 balls using optical coherence tomography," NDT&E international 34 (2001);

M. Bashkansky et al., "Subsurface defect detection in ceramics by high-speed high-resolution optical coherent tomography," Optical Letters, Vol. 22, No. 1, Jan. 1, 1997.

What is claimed is:

1. A method of improving quality of optical coherence tomography (OCT) images and detectability of sub-surface structures of a sample, comprising:
   focusing incident light on the sample via a lens;
   reducing speckle due to detected multiply scattered light (MSL) by performing an average of the detected MSL over different angles of incident light while maintaining a constant optical path length; and
   collecting backscattered light from the sample at a full resolution of the lens along an output optical path which is different from optical path of the incident light.

2. The method as in claim 1, further comprising:
    detecting the collected backscattered light.
3. The method as in claim 2, wherein the detected backscattered light collected at a full resolution of the lens is a high resolution output beam.
4. The method as in claim 1, further comprising:
    disposing a prism in the optical path of the incident light; and
    translating a prism along a hypotenuse thereof to vary the angle of incident light focused on the sample.
5. The method as in claim 1, further comprising:
    disposing a mirror in the optical path of the incident light; and
    causing a mirror to tilt in different directions to vary the angle of incident light focused on the sample.
6. The method as in claim 1, further comprising:
    disposing a phase plate in the optical path of the incident light; and
    rotating the phase plate between images to produce different MSL speckle for averaging.
7. The method as in claim 1, wherein the step of collecting the backscattered light is performed by disposing a beamsplitter in a path of the backscattered light from the sample.
8. The method as in claim 2, wherein collection of backscattered light along the output optical path allows discrimination against the speckle due to coherent MSL that reaches the detector within similar coherence length as light from a region of interest of the sample.
9. In an optical coherence tomography (OCT) system, a method of improving quality of OCT images and detectability of sub-surface structures of a sample, comprising:
    focusing incident light on the sample;
    reducing speckled noise due to detected multiply scattered light (MSL) by performing an average of the detected MSL over different angles of incident light; and
    collecting backscattered light from the sample at a full resolution of a lens, focusing the incident light on the sample, along an output optical path which is different from optical path of the incident light.
10. The method as in claim 9, further comprising:
    detecting the collected backscattered light.
11. The method as in claim 10, wherein the detected backscattered light collected at a fall resolution of the lens is a high resolution output beam.
12. An apparatus for improving quality of optical coherence tomography (OCT) images and detectability of sub-surface structures of a sample, comprising:
    means for focusing incident light on the sample;
    means for reducing speckled noise due to detected multiply scattered light (MSL) by performing an average of the detected MSL over different angles of incident light while maintaining a constant optical path length;
    means for collecting backscattered light from the sample at a full resolution of the means focusing the incident light on the sample, wherein the backscattered light is collected along an output optical path which is different from optical path of the incident light, and
    means for beamsplitting positioned between the means for focusing and the means for collecting along the optical path of the incident light for splitting the backscattered light into the different output optical path to thereby discriminate against speckle due to coherent MSL.
13. The apparatus as in claim 12, further comprising:
    means for detecting the collected backscattered light.
14. The apparatus as in claim 13, wherein the detected backscattered light collected at a full resolution of the lens is a high resolution output beam.
15. An apparatus for improving quality of optical coherence tomography (OCT) images and detectability of sub-surface structures of a sample, comprising:
    a lens for focusing incident light on the sample;
    a processor for reducing speckled noise due to detected multiply scattered light (MSL) by performing an average of the detected MSL over different angles of incident light while maintaining a constant optical path length;
    an optical device for collecting backscattered light from the sample at a full resolution of the lens along an output optical path which is different from optical path of the incident light, and
    a beamsplitter positioned between the lens and the optical device along the optical path of the incident light for splitting the backscattered light into the different output optical path to thereby discriminate against speckle due to coherent MSL.
16. The apparatus as in claim 15, further comprising:
    a detector for detecting the collected backscattered light.
17. The apparatus as in claim 15, wherein the detected backscattered light collected at a full resolution of the lens is a high resolution output beam.
18. The apparatus as in claim 16, wherein the detector is a photodetector.
19. The apparatus as in claim 15, wherein the optical device is a beamsplitter.
20. The apparatus as in claim 15, wherein the different angles of incident light to performing averaging is obtained by translating a prism along its hypotenuse.
21. The apparatus as in claim 15, wherein the different angles of incident light to performing averaging is obtained by a combination of a tilting mirror and a lens.
22. The apparatus as in claim 15, wherein the different angles of incident light to performing averaging is obtained by a phase plate disposed in an optical path of thy incident light.

* * * * *